United States Patent

Langston et al.

[11] Patent Number: 5,994,548
[45] Date of Patent: Nov. 30, 1999

[54] CRYSTALLISATION OF LEVIBUPIVACAINE AND ANALOGUES THEREOF

[75] Inventors: Marianne Langston; Benjamin Mark Skead, both of Cambridge, United Kingdom

[73] Assignee: Darwin Discovery Ltd., United Kingdom

[21] Appl. No.: 08/849,418

[22] PCT Filed: Oct. 23, 1995

[86] PCT No.: PCT/GB95/02513

§ 371 Date: Apr. 25, 1997

§ 102(e) Date: Apr. 25, 1997

[87] PCT Pub. No.: WO96/12699

PCT Pub. Date: May 2, 1996

[30] Foreign Application Priority Data

Oct. 25, 1994 [GB] United Kingdom .................... 9421476
Mar. 10, 1995 [GB] United Kingdom .................... 9504926

[51] Int. Cl.$^6$ .................................................. C07D 211/30
[52] U.S. Cl. ..................................................... 546/225
[58] Field of Search ............................................. 546/225

[56] References Cited

U.S. PATENT DOCUMENTS 4,695,576  9/1987  Ekenstam et al. ...................... 514/330

FOREIGN PATENT DOCUMENTS 1180712  2/1970  United Kingdom ................... 546/225

*Primary Examiner*—Alan L. Rotman
*Assistant Examiner*—Raymond Covington
*Attorney, Agent, or Firm*—Saliwanchik, Lloyd & Saliwanchik

[57] ABSTRACT

Levobupivacaine or an analogue thereof is prepared by reaction with a tartaric acid resolving agent in a solvent, in the presence of water and/or less 0.5 equivalents of the resolving agent.

13 Claims, No Drawings

CRYSTALLISATION OF LEVIBUPIVACAINE AND ANALOGUES THEREOF

FIELD OF THE INVENTION

This invention relates to a process for the manufacture of analgesic agents such as levobupivacaine, i.e. as substantially single enantiomers, and also analogues thereof.

BACKGROUND OF THE INVENTION

Levobupivacaine and analogues thereof such as ropivacaine are useful as local anaesthetics. These (S)-enantiomers are of increasing interest as analgesics having a higher therapeutic index than the corresponding racemates. Known syntheses have various disadvantages.

Tullar et al, J. Med. Chem. 14(9):891-2 (1971), and GB-A-1180712, describe the use of natural (R,R)-tartaric acid as the resolving agent for the separation of levobupivacaine and its antipode. 2 Molar equivalents of the base are used per molar equivalent of the acid resolving agent. For the preparation of levobupivacaine on an industrial scale, this is impractical, as the (R)-bupivacaine (R,R)-tartrate salt crystallises first, necessitating additional processing and therefore lowering the overall operating efficiency.

Further, for separation of levobupivacaine from its antipode, the method described in the prior art does not give reproducible yields of the tartrate salt, and the diastereomeric excess is variable.

This prior art does not describe a consistently reproducible process. Experiments sometimes failed, using the known conditions.

Federsel et al, Acta. Chem. Scand. B41:757–761 (1987), disclose the use of 0.52 equivalents of the resolving agent dibenzoyl tartrate, en route to the (S)-enantiomer of formula I when R=H. Water of crystallisation only is present. The resolving agent is costly.

SUMMARY OF THE INVENTION

The present invention is based on the surprising discoveries that:
1. Addition of a low concentration of water, e.g. in the range 0.1–20%, to an alcoholic resolution medium, gives a much more reproducible resolution, allows the process to be run at higher concentrations (typically 20% w/v) and yields levobupivacaine (S,S)-tartrate or its antipode at higher optical purity (typically >98% diastereomeric excess).
2. Use of less than 0.5 molar equivalents of the resolving agent, preferably 0.25 molar equivalents, yields levobupivacaine (S,S)-tartrate or its antipode at higher optical purity (typically >98% diastereomeric excess), and makes more efficient use of the resolving agent.

In addition:
3. Use of (S,S)-tartaric acid, to crystallise out the levobupivacaine (S,S)-tartrate salt first, is a more efficient procedure for the preparation of levobupivacaine.
4. Levobupivacaine (S,S)-tartrate or its antipode can be converted directly into the hydrochloride salt. This is in contrast to the prior art, which involves the less efficient procedure of forming the desired hydrochloride from free base.

These discoveries can be utilised in connection with all compounds of the formula in claim 1, i.e. pipecolic acid 2,6-dimethylanilide or a N-alkyl derivative. They include optically-enriched bupivacaine, especially levobupivacaine, and ropivacaine.

DESCRIPTION OF THE INVENTION

The novel process is preferably conducted in accordance with all the parameters given above. In other respects, conventional crystallisation technology may be used. The reaction is preferably conducted using a $C_{1-6}$ alkanol, such as isopropanol, as the primary reaction solvent, but any suitable water-miscible organic solvent may be used.

This invention is conveniently operated in conjunction with a racemisation process. Levobupivacaine and its antipode, and analogues thereof, in free base form or as its salts, can be racemised, as described in International Patent Application No. PCT/GB95/02247, as part of an efficient recycle procedure.

The following Examples illustrate the invention.

EXAMPLE 1

Bupivacaine hydrochloride monohydrate (1 kg, 2.916 mol) was charged to a separator with water (5 l) and TBME (5 l). Sodium hydroxide solution (10 N, 300 ml, 3 mol) was then added, and the reaction mixture was stirred for 5 min until all the solids had dissolved. The stirrer was stopped and the layers were allowed to separate over 0.5 h. The aqueous layer was separated and the organic layer was washed with water (2 l). The organic layer was charged to a vessel configured for atmospheric distillation. TBME (2.5 l) was distilled. Isopropanol was added and the distillation continued until all the TBME had been removed. The total volume of isopropanol remaining should be 4200 ml (1 part bupivacaine base: 5 parts isopropanol). Water (105 ml) and then (S,S)-(-)-tartaric acid (109 g, 0.73 mol, 0.25 eq) were added at 80° C., and the mixture was stirred at 80° C. until all the solids had dissolved.

The solution was allowed to cool to 20° C., with slow stirring. If crystallisation had not started when the temperature had reached 65° C. then the solution was seeded. The crystals were filtered off and washed twice with isopropanol (2×500 ml) and then dried in vacuo to give levobupivacaine (S,S)-tartrate (430 g, 80% yield of desired diastereomer at 98% e.e.).

EXAMPLE 2

Levobupivacaine (S,S)-tartrate (50 g, 0.069 mol) was suspended in isopropanol (150 ml) and heated to 50° C. Hydrogen chloride (5 g, 0.14 mol) gas was introduced. The temperature rose to 65° C. and the solids dissolved. The mixture was heated to 80° C. to ensure complete dissolution. The mixture was cooled to 5° C. and a solid crystallised. The solid was filtered off and washed with isopropanol (2×50 ml) and dried in vacuo to give levobupivacaine hydrochloride (21.9 g, 40%).

EXAMPLES 3–14 AND COMPARATIVE EXAMPLE A

In order to investigate the criticality of the presence of water and the relative amounts of the compounds of formula (I) and resolving agent, various comparative tests were done. In each of the tests, to racemic bupivacaine free base (20 g) were added IPA (isopropanol; 5 vol) and the given amount of water. The suspension was warmed with stirring. At approximately 75° C., the given amount of tartaric acid was added. The suspension was brought to reflux. Once all the solid had dissolved, the solution was allowed to cool slowly to room temperature. The suspension was filtered and the cake obtained sampled; the sample was treated with aqueous NaOH and the ee of the liberated free base measured by chiral HPLC. The cake was washed with IPA (20 ml). The solid was dried to constant weight in a vacuum oven at 40–50° C.

The results are tabulated below, in respective groups of 5 and 4 tests (each showing the effect of varying the amount of water), and 4 and 3 tests (each showing the effect of varying the amount of resolving agent).

TABLE

| Example | No. equiv. tartaric acid | % Water | % ee after filtration | % ee after wash | yield (g) |
|---|---|---|---|---|---|
| A | 0.5 | 0 | 8.5 | 38 | 18.9 |
| 3 | 0.5 | 1 | 38 | 47 | 16.4 |
| 4 | 0.5 | 2 | 82 | 98 | 12 |
| 5 | 0.5 | 3 | 92 | 98 | 11 |
| 6 | 0.5 | 5 | 95 | 99 | 10.2 |
| 7 | 0.4 | 0 | 31 | 46 | 17.9 |
| 8 | 0.4 | 1 | 48 | 58 | 15.4 |
| 9 | 0.4 | 2 | 76 | 88 | 12.4 |
| 10 | 0.4 | 3 | 85 | 95 | 11.4 |
| A | 0.5 | 0 | 8.5 | 38 | 18.9 |
| 11 | 0.4 | 0 | 31 | 46 | 17.9 |
| 12 | 0.3 | 0 | 72 | 84 | 12.9 |
| 13 | 0.2 | 0 | 66 | 85 | 9.9 |
| 3 | 0.5 | 1 | 38 | 47 | 16.4 |
| 8 | 0.4 | 1 | 48 | 58 | 15.4 |
| 14 | 0.3 | 1 | 86 | 96 | 11.6 |

We claim:

1. A process for preparing an optically-enriched compound of formula (I)

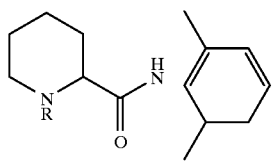

(I)

wherein R is n-butyl, which comprises reacting a mixture of enantiomers of a compound of formula I with a tartaric acid resolving agent in a water-miscible organic solvent medium, wherein said organic solvent medium comprises from about 0.1 to 20% water.

2. A process for preparing an optically-enriched compound of formula (I)

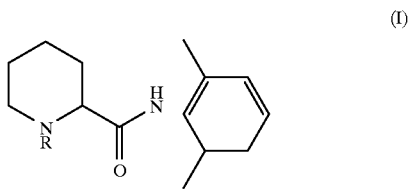

(I)

wherein R is n-butyl, which comprises reacting a mixture of enantiomers of a compound of formula (I) with a tartaric acid resolving agent in a water miscible organic solvent medium, wherein the reaction is conducted in the presence of less than about 0.5 equivalents, per molar equivalent of the compound of formula (I), of the resolving agent.

3. The process, according to claim 2, wherein said organic solvent medium comprises from about 0.1 to 20% water.

4. The process, according to claim 1, wherein said resolving agent is (S,S)-tartaric acid.

5. The process, according to claim 1, wherein said solvent comprises a $C_{1-6}$ alkanol.

6. The process, according to claim 1 which comprises using between about 0.2 and 0.5 molar equivalents of said resolving agent, per molar equivalent of the compound of formula (I).

7. The process, according to claim 1 which additionally comprises conversion of the optically-enriched compound to the hydrochloride salt.

8. The process., according to claim 1, for preparing levobupivacaine.

9. The process, according to claim 2, wherein said resolving agent is (S,S)-tartaric acid.

10. The process, according to claim 2, wherein said solvent comprises a $C_{1-6}$ alkanol.

11. The process, according to claim 2, which comprises using between about 0.2 and 0.5 molar equivalents of said resolving agent, per molar equivalent of the compound of formula (I).

12. The process, according to claim 2, which additionally comprises conversion of the optically-enriched compound to the hydrochloride salt.

13. The process, according to claim 2, for preparing levobupivacaine.

* * * * *

UNITED STATES PATENT AND TRADEMARK OFFICE
CERTIFICATE OF CORRECTION

PATENT NO. : 5,994,548
DATED : November 30, 1999
INVENTOR(S) : Marianne Langston, et. al.

It is certified that error appears in the above-identified patent and that said Letters Patent is hereby corrected as shown below:

Column 3, line 45: "formula I" should read --formula (I)--.

Column 4, line 25: "claim 1" should read --claim 1,--.

Column 4, line 29: "claim 1" should read --claim 1,--.

Column 4, line 32: "process.," should read --process,--.

Signed and Sealed this

Twelfth Day of September, 2000

Attest:

Q. TODD DICKINSON

Attesting Officer

Director of Patents and Trademarks